US007951105B2

United States Patent
Medow et al.

(10) Patent No.: US 7,951,105 B2
(45) Date of Patent: May 31, 2011

(54) MEDICAL SHUNT/VALVE FOR REGULATION OF BODILY FLUIDS

(75) Inventors: Joshua E. Medow, Madison, WI (US); Christopher C. Luzzio, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 683 days.

(21) Appl. No.: 10/570,738

(22) PCT Filed: Aug. 17, 2004

(86) PCT No.: PCT/US2004/026703
§ 371 (c)(1),
(2), (4) Date: Mar. 6, 2006

(87) PCT Pub. No.: WO2005/025640
PCT Pub. Date: Mar. 24, 2005

(65) Prior Publication Data
US 2007/0032757 A1    Feb. 8, 2007

Related U.S. Application Data

(60) Provisional application No. 60/501,358, filed on Sep. 9, 2003.

(51) Int. Cl.
*A61M 5/00* (2006.01)
(52) U.S. Cl. .......................................... 604/9; 604/247
(58) Field of Classification Search ........ 604/4.01–6.16, 604/8–10, 246–255
See application file for complete search history.

(56) References Cited

U.S. PATENT DOCUMENTS

| | | | |
|---|---|---|---|
| 3,288,142 A | 11/1966 | Hakim | |
| 3,991,768 A | 11/1976 | Portnoy | |
| 4,103,689 A | 8/1978 | Leighton | |
| 4,382,445 A | 5/1983 | Sommers | |
| 4,500,311 A | 2/1985 | Redmond et al. | |
| 4,551,128 A | 11/1985 | Hakim et al. | |
| 4,595,390 A | 6/1986 | Hakim et al. | |
| 4,605,395 A | 8/1986 | Rose et al. | |
| 4,673,384 A * | 6/1987 | Marion | 604/10 |
| 4,731,056 A | 3/1988 | Tremulis | |
| 4,772,257 A | 9/1988 | Hakim et al. | |
| 4,795,437 A | 1/1989 | Schulte et al. | |
| 4,867,741 A | 9/1989 | Portnoy | |
| 5,000,731 A | 3/1991 | Wong et al. | |
| 5,167,615 A | 12/1992 | East et al. | |
| 5,176,627 A | 1/1993 | Watson | |
| 5,192,265 A * | 3/1993 | Drake et al. | 604/10 |
| 5,387,188 A | 2/1995 | Watson | |

(Continued)

*Primary Examiner* — Tatyana Zalukaeva
*Assistant Examiner* — Philip R Wiest
(74) *Attorney, Agent, or Firm* — Criag A. Fieschko, Esq.; DeWitt Ross & Stevens S.C.

(57) ABSTRACT

Shunts (valves) (100) for controlled flow of bodily fluids, such as cerebrospinal fluid, include a valve actuating member (114) (such as a piston (120)) between inlet (108) and outlet (110) ports. The valve actuating member is biased toward a state wherein the valve is closed, and it includes a face adjacent the upstream side of the valve (and preferably isolated from the downstream side of the valve) whereby fluid pressure in the upstream side exerts an opening force on the face to urge the valve toward an open state. When the opening force on the valve exceeds the closing force by some amount, the valve actuating member moves the valve to the open state, allowing fluid flow through the fluid passage between the inlet and outlet ports.

47 Claims, 3 Drawing Sheets

U.S. PATENT DOCUMENTS

| | | | |
|---|---|---|---|
| 5,405,316 A | 4/1995 | Magram | |
| 5,540,668 A * | 7/1996 | Wilson et al. | 604/248 |
| 5,634,894 A | 6/1997 | Magram | |
| 5,637,083 A | 6/1997 | Bertrand et al. | |
| 5,643,195 A * | 7/1997 | Drevet et al. | 604/9 |
| 5,913,852 A | 6/1999 | Magram | |
| 6,090,062 A | 7/2000 | Sood et al. | |
| 6,264,625 B1 | 7/2001 | Rubenstein et al. | |
| 6,336,924 B1 | 1/2002 | Lecuyer et al. | |
| 6,379,340 B1 * | 4/2002 | Zinger et al. | 604/246 |
| 6,383,160 B1 | 5/2002 | Madsen | |
| 6,474,360 B1 | 11/2002 | Ito | |
| 6,485,449 B2 | 11/2002 | Ito | |
| 6,565,525 B1 * | 5/2003 | Burbank et al. | 604/93.01 |
| 6,575,928 B2 | 6/2003 | Saul et al. | |
| 7,025,742 B2 * | 4/2006 | Rubenstein et al. | 604/9 |
| 2003/0004495 A1 | 1/2003 | Saul | |

* cited by examiner

FIG. 1

MEDICAL SHUNT/VALVE FOR REGULATION OF BODILY FLUIDS

CROSS-REFERENCE TO RELATED APPLICATIONS

This application claims priority under 35 USC §119(e) to U.S. Provisional Patent Application 60/501,358 filed 9 Sep. 2003, the entirety of which is incorporated by reference herein.

FIELD OF THE INVENTION

This document concerns an invention relating generally to medical shunts for controlling the flow of body fluids, e.g., shunts for drainage of cerebrospinal fluid for treatment of hydrocephalus and similar conditions.

BACKGROUND OF THE INVENTION

Numerous physiological processes rely on a proper balance between generation and disposal of bodily fluids. As an example, within the body, the brain and spinal cord are bathed in cerebrospinal fluid, which helps maintain their proper operation. Large cavities within the brain, the ventricles, produce and reabsorb the cerebrospinal fluid so that it is regularly replaced for healthy operation of the body's neurological system. However, in some cases an imbalance occurs between the rate of fluid production and the rate of reabsorption. This can lead to hydrocephalus, a condition wherein the brain's ventricles become enlarged with cerebrospinal fluid, pressing brain tissue against the skull. This can lead to serious neurological problems, and potentially death.

The most effective treatment for hydrocephalus is surgical insertion of a shunt, a valve which vents excess cerebrospinal fluid from the brain. A neurosurgeon makes an estimate of the amount of flow required to relieve hydrocephalus, and selects a shunt having the desired flow capacity. A flap is cut in the scalp, a small hole is drilled in the skull, and a catheter is inserted to pass into a ventricle of the brain. The catheter is then connected to the shunt beneath the scalp. Another catheter is attached to the outlet of the shunt and is usually tunneled into the skin, down the neck, and into the peritoneal (abdominal) cavity. The scalp is then sewn shut over the shunt, which vents the excess cerebrospinal fluid to the peritoneal cavity for absorption. When a shunt is installed in this manner, it is generally referred to as a ventriculoperitoneal (VP) shunt. Shunts can also be installed to drain from the ventricles into the venous system or other receptive body cavities; further, shunts are also sometimes used to regulate the flow of liquids from structures other than the brain.

Common shunts are subject to numerous problems which designers have long sought to overcome, such as problems with tissue ingrowth and fouling, plaque buildup, and size and cost issues. Control of shunt valve response characteristics (i.e., flow volume vs. pressure characteristics) remains a major issue, with common problems being that response characteristics may undesirably change over time, and it is often difficult to easily adjust the response characteristics of a shunt to suit the needs of individual patients. Another common problem is the tendency for a shunt valve to open once a static threshold pressure difference is present, but then remain partially open after this static pressure difference is relieved. This effect arises owing to the dynamic pressure of fluid flow, and can (for example) result in unnecessary drainage at of cerebrospinal fluid at lower than desired pressures in the ventricles.

Another disadvantage of many shunts is that they operate in the manner of a common check valve, wherein their flow is dependent on the pressure difference across the valve between its inlet and outlet. When the pressure difference exceeds some threshold level, the valve opens to allow cerebrospinal fluid to drain from the brain. This arrangement can lead to the problem of siphoning: since opening of the valve is in part dependent on the pressure at the valve outlet, low pressure on the outlet side may cause the valve to open even if the pressure on the inlet side is not indicative of excess cerebrospinal fluid pressure in the ventricles. Thus, if a patient repositions his/her head with respect to the rest of his/her body—for example, by standing up from a supine position—decreased pressure in the peritoneal cavity can increase the pressure difference to such an extent that the valve opens and unnecessarily drains cerebrospinal fluid.

A further disadvantage of many shunts is that they allow reversible flow, i.e., they can allow backflow from the peritoneal cavity to the brain if the (downstream) pressure in the peritoneal cavity should for some reason exceed the (upstream) pressure in the brain by the same threshold pressure difference (though in this case the pressure difference is reversed between the upstream and downstream sides). This is naturally undesirable since it can cause a sudden increase in fluid pressure on the brain, whereas a sudden increase in fluid pressure in the peritoneal cavity is generally not critical.

SUMMARY OF THE INVENTION

The invention, which is defined by the claims set forth at the end of this document, is directed to methods and apparata which at least partially alleviate the aforementioned problems. A basic understanding of some of the preferred features of the invention can be attained from a review of the following brief summary of the invention, with more details being provided elsewhere in this document.

A shunt for use in the maintenance of proper pressure of cerebrospinal or other body fluids includes an inlet port, an outlet port, and a fluid passage therebetween. A valve is situated between the inlet and outlet ports, thereby defining an upstream side of the fluid passage between the inlet port and the valve, and a downstream side of the fluid passage between the valve and the outlet port. A movable valve actuating member (such as a piston) is provided, with the valve actuating member being biased by a closing force to urge the valve toward a closed state. The valve actuating member has a face adjacent the upstream side of the fluid passage (and isolated from the downstream side of the fluid passage), wherein fluid pressure in the upstream side exerts an opening force on the face and urges the valve toward an open state. When the opening force on the valve actuating member exceeds the closing force by some amount, the valve actuating member moves the valve to the open state, allowing fluid flow through the fluid passage between the inlet and outlet ports. Thus, for example, where the valve actuating member is a piston having a piston face adjacent the upstream side of the fluid passage, the valve will open once some shunting pressure arises on the upstream side which is sufficient to overcome the closing force. A particularly valuable aspect of this arrangement is that the valve of the shunt does not open in response to the pressure on the downstream side of the fluid passage (e.g., in the peritoneal cavity), and instead will only open in response to the pressure at the upstream side of the fluid passage (e.g., in the ventricles), as measured versus the opposing pressure generated by the closing force. More simply stated, the opening of the valve is decoupled from the pressure across the valve (and the downstream pressure in the peritoneal cavity), and is instead made dependent on the upstream pressure in the ventricles, so that siphoning will not occur when pressure in the peritoneal cavity drops.

The valve actuating member preferably takes the form of a displaceable piston, wherein the piston may include a cutout (such as a through-hole or groove) which partially defines the valve: as the cutout moves into alignment with the fluid passage (e.g., with a drain port defined at the start of the downstream side of the fluid passage), the valve is switched to its open state and fluid may flow from the upstream side to the downstream side. Alternatively, the cutout may be provided in a mask, such as an elastic membrane, which may be linked to the piston such that the piston moves the mask (and its cutout) into and out of alignment with the fluid passage to open and close the valve. A flexible mask is particularly beneficial because it can conform to tightly seal the juncture between the upstream and downstream sides of the fluid passage unless the cutout is moved into alignment with the passage. For example, where the mask is an elastic membrane situated between the upstream side of the fluid passage and a drain port on the downstream side, the fluid pressure on the upstream side may ordinarily push the membrane to bulge into the drain port (when its cutout is not aligned with the drain port), ensuring a tight seal against fluid leakage.

The closing force biasing the valve towards the closed state is preferably provided by an elastic diaphragm connected to the piston (and which may define at least a portion of the piston face), or by a mechanical spring (e.g., leaf or helical spring), pneumatic spring, or the like. If an elastic diaphragm is used, it may beneficially be bounded on one of its sides by a closed gas chamber containing compressible gas, whereby the pressure within the gas chamber contributes (along with the elasticity of the diaphragm) to the closing force. If the gas chamber is constructed so that it has selectively adjustable volume—as by defining it as a cylinder into which a cap may be screwed to reduce its volume—a user may selectively adjust the gas chamber volume to adjust the pressure of gas therein, and thereby adjust the closing force.

Where the valve actuating member is provided by a displaceable piston which travels along a linear bore, the bore is preferably oriented at least substantially perpendicular to the direction in which fluid flows between the upstream and downstream sides of the flow passage. As a result, fluid flow through the valve will not tend to displace the piston such that the valve is urged towards the closed or open state.

Further advantages, features, and objects of the invention will be apparent from the following detailed description of the invention in conjunction with the associated drawings.

DETAILED DESCRIPTION OF PREFERRED EMBODIMENTS OF THE INVENTION

Several preferred versions of the invention will now be reviewed. Initially referring to FIG. 1, a first basic version of a shunt is depicted generally by the reference numeral 100. The shunt 100 includes an inner body 102 separated from an outer casing 104 by a gas chamber 106, with the inner body 102 being supported within the outer casing 104 by an inlet port 108 and an outlet port 110. The inlet port 108 protrudes from the outer casing 104, and may be connected to an inlet catheter (not shown) leading the ventricles of a brain. The outlet port 110 similarly protrudes from the outer casing 104, and may be connected to an outlet catheter leading to the peritoneal cavity or some other site for receiving cerebrospinal fluid.

Figure 1:
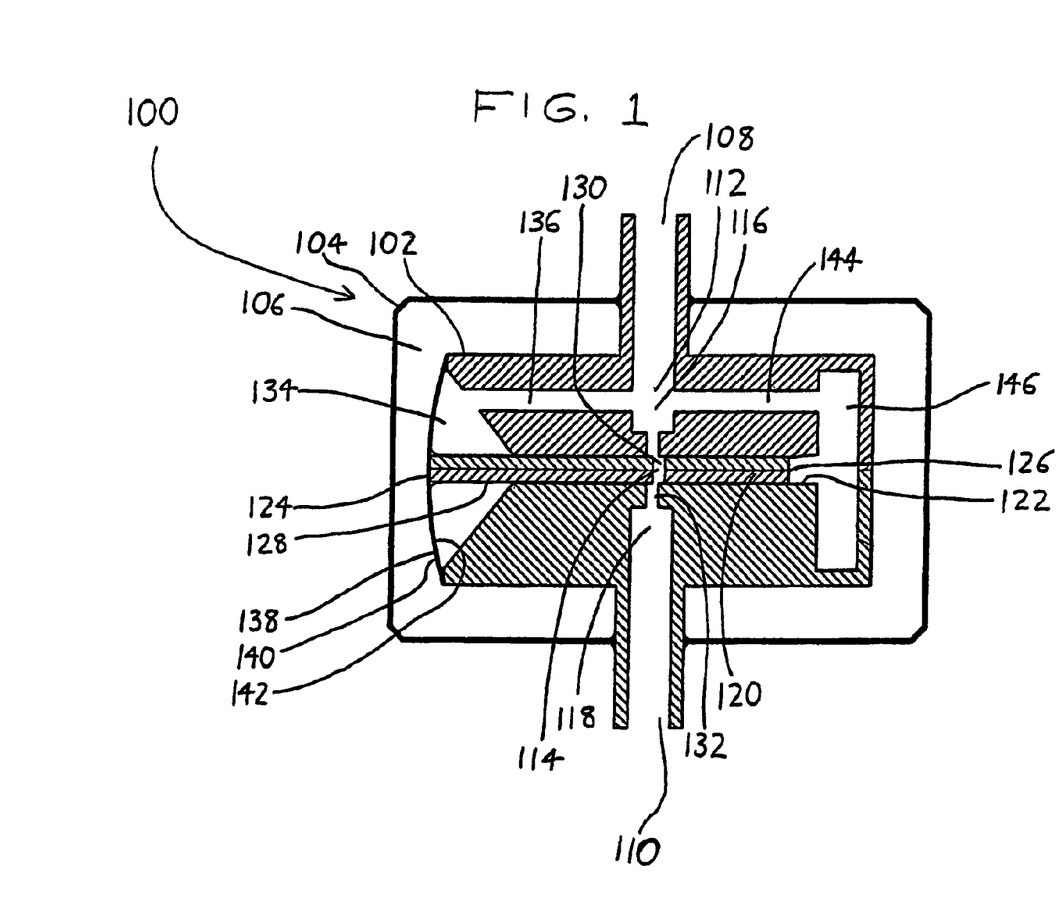
FIG. 1 is a schematic cross-sectional view of a first exemplary shunt 100.

A fluid passage 112 extends between the inlet port 108 and outlet port 110 to allow flow of cerebrospinal fluid therebetween. However, such flow is not unregulated; a valve 114 (i.e., an openable and closable gate) opens and closes the fluid passage 112 to normally block flow of cerebrospinal fluid, and to allow flow when some shunting pressure is reached at the inlet port 108. The valve 114 may be regarded as separating the fluid passage 112 into an upstream side 116 between the inlet port 108 and the valve 114, and a downstream side 118 between the valve 114 and the outlet port 110.

The valve 114 is defined in the fluid passage 112 by a piston 120 which slides linearly within a bore 122 defined in the inner body 102, with the bore 122 intersecting the fluid passage 112. The piston 120 has a first end 124 and an opposing second end 126, with an intermediate length 128 extending therebetween. This intermediate length 128 has a cutout 130 defined therein, with the cutout 130 taking the form of a through-hole, circumferential groove, or other discontinuity in the piston 120. Thus, the cutout 130 allows cerebrospinal fluid to pass between the upstream side 116 and a drain port 132 at the outset of the downstream side 118 when the cutout 130 is aligned with the fluid passage 112. Otherwise, when the cutout 130 does not at least partially rest within the fluid passage 112, the intermediate length 128 of the piston 120 blocks the fluid passage 112. The piston 120 thus serves as a valve actuating member such that when the piston 120 is appropriately displaced within the bore 122, the valve 114 will change between open and closed states to allow or block passage of cerebrospinal fluid from the inlet port 108 to the outlet port 110.

Looking then to the arrangement by which the piston 120 is made to actuate the valve 114, it is seen that the upstream side 116 of the fluid passage 112 is connected to a first piston actuation chamber 134 via a first fluid communication channel 136. The bore 122 of the piston 120 opens onto the first actuation chamber 134 such that the piston 120 extends therein. A deformable elastic diaphragm 138 separates the first actuation chamber 134 (and any fluid therein) from the gas chamber 106, so that the diaphragm 138 has a fluid side 140 bounding the fluid in the first actuation chamber 134 and a gas side 142 bounding the gas in the gas chamber 106. The first end 124 of the piston 120 is affixed to the diaphragm 138 in such a manner that flexure of the diaphragm 138 in directions generally parallel to the bore 122 will cause the piston 120 to translate within the bore 122. A second fluid communication channel 144 also leads from the upstream side 116 of the fluid passage 112 to a second piston actuation chamber 146 onto which the bore 122 opens, with the piston second end 126 facing the second actuation chamber 146. Thus, it can be seen that the piston 120 effectively has three faces (i.e., three surfaces upon which pressure may act to displace the piston 120 within its bore 122): two opening faces which may be driven to open the valve 114, a first opening face defined by the fluid side 140 of the attached diaphragm 138 and a second opening face defined by the piston second end 126; and one closing face which may be driven to close the valve, the gas side 142 of the attached diaphragm 138 (or viewed differently, the first end 124 of the piston 120 and the gas side 142 of the diaphragm 138 attached thereon).

The elasticity of the diaphragm 138, plus the gas pressure within the gas chamber 106 acting on the closing face 142 of the piston 120, will maintain the valve 114 in an ordinarily closed state. However, when the pressure in the upstream side 116 of the fluid passage 112 (and thus in the first actuation chamber 134 and second actuation chamber 146) acts on the first and second opening faces 126 and 140 to overcome the opposing biasing force of the elastic diaphragm 138 and the opposing pressure in the gas chamber 106 on the closing face 142, the piston 120 may displace in the bore 122 to a sufficient extent that the cutout 130 aligns with the fluid passage 112, thereby allowing fluid flow between the upstream side 116 and a downstream side 118 of the fluid passage 112. Conversely, when the pressure within the upstream side 116 drops to such a degree that the pressures acting on the faces 126 and 140 are less than the opposing pressures generated by the gas chamber 106 and the elasticity of the diaphragm 138, the piston 120 will displace so that the cutout 130 is no longer aligned with the fluid passage 112, thereby closing the valve 114.

A valuable feature of the foregoing arrangement is that the opening of the valve 114 is wholly or largely decoupled from the pressure in the outlet port 110, and thus in the peritoneal cavity or other drainage location. Since the faces 126 and 140 of the piston 120 which are driven to open the valve 114 are solely exposed to the upstream side 116 of the fluid passage 112, the opening of the valve is dependent on the pressure at the inlet port 108 (and thus within the brain ventricles) and the valve opening force generated thereby, versus the valve closing force generated by the elasticity of the diaphragm 138 and the pressure within the gas chamber 106. Thus, appropriate choice of the elasticity of the diaphragm 138, and the pressure within the gas chamber 106, will determine the closing pressure opposing the opening pressure within the upstream side 116 of the shunt 100. FIG. 1, being a simplified schematic view of the exemplary shunt 100, does not illustrate convenient means by which the tension of the diaphragm 138 and the pressure of the gas chamber 106 may be varied. However, numerous means for allowing such variance can be provided. As a first example, shunts such as the shunt 100 can be manufactured with a variety of diaphragms 138 having different tensions (as by providing different diaphragm thicknesses). Medical personnel may then choose a diaphragm 138 having a desired tension, its attached piston 120 may be slid into the bore 122, and the diaphragm may be fit atop the first actuation chamber 134 and have its edges folded about the edges of the inner body 102 and sealed thereon, as by fitting a rubber ring about the diaphragm 138 and inner body 102. The gas pressure within the gas chamber 106 may be conveniently varied by providing a screw-on cap having a threaded engagement about an end of the outer casing 104, whereby screwing on the cap reduces the volume of the gas chamber 106 (and thereby increases the pressure therein). Alternatively, some form of structure which may be adjustably extended from the exterior of the outer casing 104 to its interior (e.g., a threaded fastener extending from the exterior of the outer casing 104 to its interior) may be adjusted to extend into the interior of the gas chamber 106 by a desired degree such that the gas pressure within the gas chamber 106 is set as desired.

Another beneficial feature of the foregoing arrangement is that the displacement of the valve actuating member, i.e., the piston 120, is oriented perpendicular to the direction of flow through the fluid passage 112 (and more particularly through the valve 114). As a result, once flow through the valve 114 is initiated, dynamic pressures will not tend to effect displacement of the piston 120. Thus, the shunt 100 overcomes difficulties encountered in some prior shunts wherein their valves remain open even after some threshold opening pressure is relieved, thereby leaving their valves open at some undesirable range of lower pressures.

Figure 2:
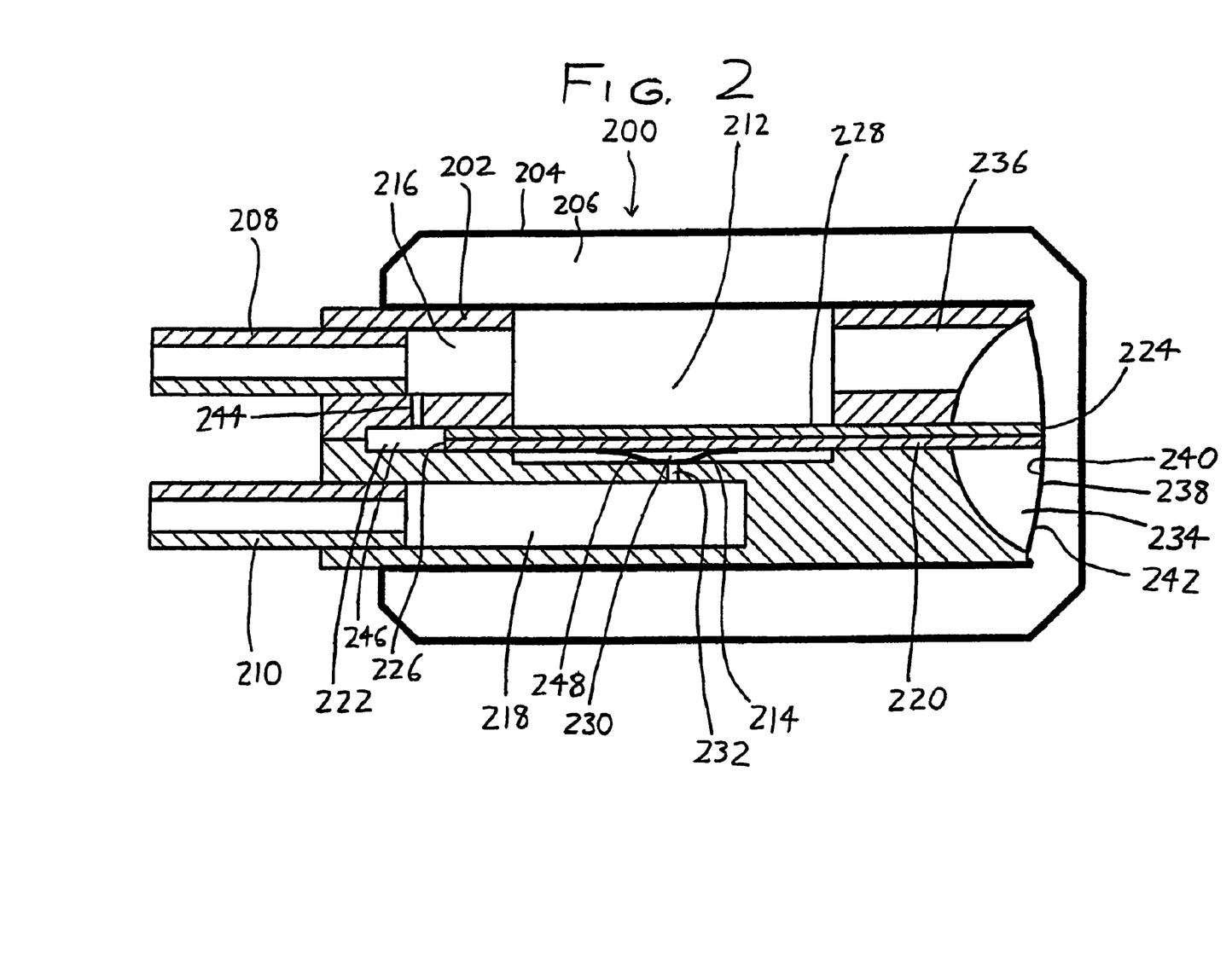
FIG. 2 is a schematic cross-sectional view of a second exemplary shunt 200.

An alternative shunt 200 is then shown in FIG. 2. The shunt 200 also includes an inner body 202 and outer casing 204 spaced by a gas chamber 206. The inner body 202 here includes an inlet port 208 and an outlet port 210 extending from one end of the casing 204, which can in some cases be a more convenient arrangement for installation in or on a body. A fluid passage 212 extends between the inlet port 208 and outlet port 210, with a valve 214 separating the fluid passage 212 into an upstream side 216 between the inlet port 208 and the valve 214, and a downstream side 218 between the valve 214 and the outlet port 210. The valve 214 is here partially defined by a mask 248 affixed to the intermediate length 228 of a piston 220, which slides linearly within a bore 222 defined in the inner body 202 and intersects the fluid passage 212. The mask 248 is situated between the upstream side 216 of the fluid passage 212 and a drain port 232 defined at the outset of the downstream side 218, and it slides across the drain port 232 when the piston 220 is displaced. The mask 248 is preferably formed of a flexible, deformable membrane which bears against and normally closes the drain port 232 from the upstream side 216 of the fluid passage 212. However, the mask 248 bears a cutout 230 (such as a narrow slit) whereby the valve 214 opens when the cutout 230 aligns with the drain port 232 of the fluid passage 212. By providing the cutout 230 on a flexible mask 248 on the piston 220 rather than on the piston 220 itself (as in the shunt 100 of FIG. 1), valve leakage might be diminished because the mask 248 may be made to ordinarily bear on and seal the drain port 232, with its bearing force being enhanced by fluid pressure in the upstream side 216 of the fluid passage 212. However, fluid will be allowed to pass when the cutout 230 and drain port 232 are aligned.

The piston 220 is then actuated in much the same manner as in the shunt 100 of FIG. 1. The piston 220 has a first end 224 extending into a first piston actuation chamber 234 and being affixed to a deformable elastic diaphragm 238, and a first fluid communication channel 236 connects the upstream side 216 of the fluid passage 212 to the first piston actuation chamber 234. The opposing piston second end 226 rests adjacent a second piston actuation chamber 246 defined within the bore 222, and the second piston actuation chamber 246 is also connected to the upstream side 216 of the fluid passage 212 by a second fluid communication channel 244. The piston 220 thus has three effective faces (i.e., three surfaces upon which pressure may act to displace the piston 220 within its bore 222): a first opening face 240 defined by the fluid side of the diaphragm 238 (the side adjacent the fluid in the first piston actuation chamber 234); a second opening face 226 (defined by the piston second end 226); and a closing face 242 defined by the gas side of the diaphragm 238 (the side adjacent the gas in the gas chamber 206). The gas pressure on the closing face 242, plus the elasticity of the diaphragm 238, ordinarily maintains the valve 214 in a closed state. However, when the pressure in the upstream side 216 of the fluid passage 212 reaches a shunting pressure sufficient to urge the first opening face 240 and second opening face 226 of the piston 220 far enough to align the cutout 230 of the mask 248 with the fluid passage 212, fluid flow between the upstream side 216 and downstream side 218 will occur. When pressure at the upstream side 216 drops below the shunting pressure, the piston 220 and its mask 248 (with cutout 230) move out of alignment with the fluid passage 212 to return the valve 214 to its closed state. As with the shunt 100 of FIG. 1, the opening of the valve 200 is independent of the fluid pressure at the downstream side 218, and valve actuation is effected by actuation of the piston 220 in a direction perpendicular to fluid flow, thereby avoiding any tendency for the valve 214 to remain open once pressure at the upstream side 216 drops below the shunting pressure.

Figure 3:
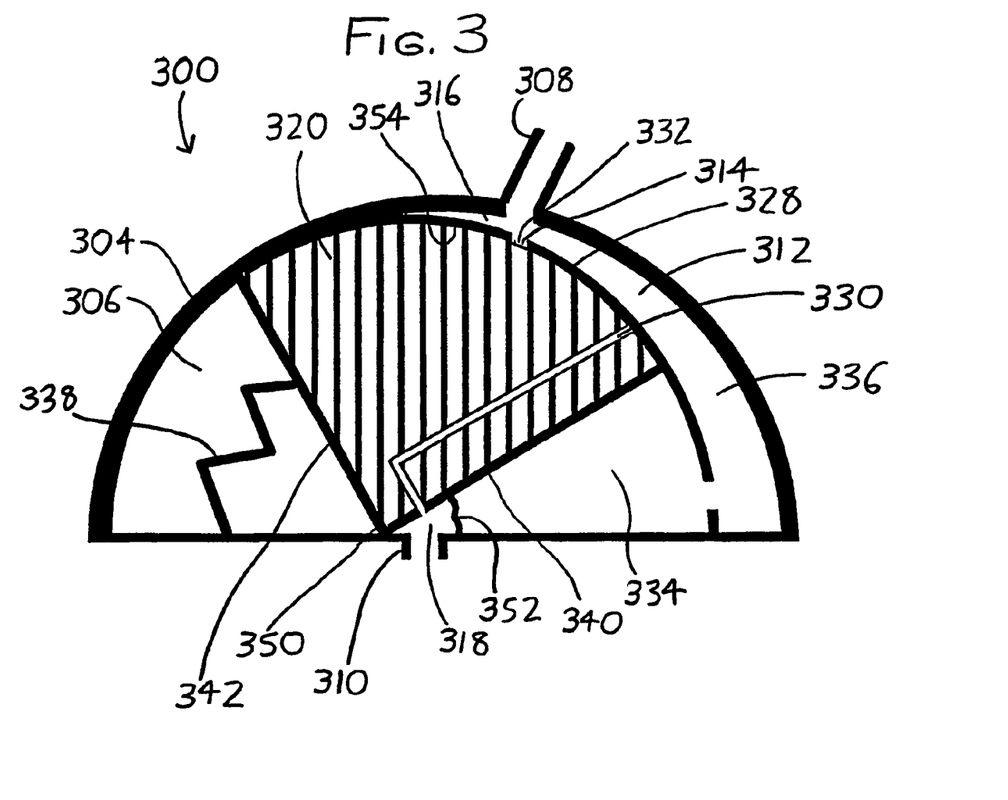
FIG. 3 is a schematic cross-sectional view of a third exemplary shunt 300.

It is notable that the principles of the foregoing shunts can be extended to nonlinear piston/bore arrangements, for example, to rotary piston arrangements. To illustrate, FIG. 3 illustrates a third version of a shunt, depicted generally by the reference numeral 300, wherein a generally semicylindrical casing 304 bears an inlet port 308 and an outlet port 310 with a fluid passage 312 extending therebetween. Within the casing 304, a valve 314, which is part defined by a piston 320, divides the fluid passage 312 into an upstream side 316 adjacent the inlet port 308 and a downstream side 318 adjacent the outlet port 310. As in the prior shunts 100 and 200, the valve 314 acts to selectively allow fluid flow from the inlet port 308 and upstream side 316 to the downstream side 318 and outlet port 310, but a somewhat different arrangement is used to effect such selective flow.

Initially, the piston 320 is more in the nature of a rotary piston, i.e., it is actuated via a pivoting or rotating motion. The piston 320 has opposing faces 340 and 342, with the piston being pivotally movable about a fulcrum 350 situated between the faces 340 and 342 on one side and the faces 340 and 342 being bounded by an intermediate length 328 on the opposite side. The intermediate length 328 has a curved profile conforming to a section of a cylinder, and it complementarily slides against a portion of the casing 304 and also against an inner guide wall 354, which has a drain port 332 defined adjacent the inlet port 308. The piston 320 also includes a cutout 330 extending from its intermediate length 328 from a point adjacent face 340 to a point on face 340 adjacent the outlet port 310 and fulcrum 350, with the cutout 330 being unobstructed at the downstream side 318 of the fluid passage 312, and being normally obstructed (closed) at the upstream side 316 by the inner guide wall 354 unless the cutout 330 moves into alignment with the drain port 332 (in which case the valve 314 is placed in the open state to allow fluid flow between the upstream side 316 and downstream side 318).

The following arrangement is then used to pivot the piston 320 of the valve 314 between the open and closed states. The piston 320 is connected by a flexible skirt 352 to define a gas chamber 306 bounded by the casing 304, the face 342 of the piston 320, and the skirt 352. The pressure of the gas on the piston face 342 will normally bias the valve 314 to the closed state (wherein the intermediate length 328 of the piston 320 obscures the drain port 332), and a spring 338 may also be provided between the casing 304 and the piston face 342 to provide additional biasing force. On the side of the piston 342 opposite this valve closing face 342, the piston face 340 acts as a valve opening face. A fluid communication channel 336 extends from the inlet port 308 between the casing 304 and the inner guide wall 354 to open upon a piston actuation chamber 334 between the inner guide wall 354 and the opening face 340. Fluid entering the inlet port 308 may therefore flow into the piston actuation chamber 334, and if it reaches a shunting pressure, it may pivotally displace the piston 342 to such an extent that the cutout 330 is adjacent the drain port 332, thereby opening the valve 314 and allowing fluid flow between the upstream side 316 and downstream side 318. Otherwise, if the pressure at the inlet port 308 and upstream side 316 (and thus in the piston actuation chamber 334) is insufficient, the piston 320 is biased by the gas pressure and spring 338 force in the gas chamber 306 to maintain the drain port 332 obscured by the intermediate length 328 of the piston 320.

All of the foregoing shunts are of course preferably formed of biocompatible materials, and are appropriately sized, shaped, and configured for implantation (if they are to be used after implantation). The appropriate choice of materials, sizes, configurations, etc. to be used in any given situation will be apparent to surgeons and other medical personnel who work with shunts, and to others who are familiar with shunts.

Various preferred versions of the invention have been discussed above (and are shown in the appended papers) to illustrate different possible features of the invention and the varying ways in which these features may be combined. Apart from combining the different features of the foregoing versions of the invention in varying ways, other modifications are also considered to be within the scope of the invention. Following is an exemplary list of such modifications.

Initially, it is notable that numerous modified versions of the foregoing shunts can be constructed wherein the valve closing and/or opening forces are provided by different arrangements, and/or wherein the shunts are simplified in some respect. As an example, with regard to the shunt 100, the second communication channel 144 and actuation chamber 146 could be eliminated, and the bore 122 can simply open onto the gas chamber 106 at this location so that the piston 120 may extend into and out of the gas chamber 106 as it displaces. In this case, since the pressure of the gas chamber 106 on the first and second ends of the piston 124 and 126 balance, displacement of the piston 120 would primarily be determined by the relative pressures between the fluid side 140 and gas side 142 of the diaphragm 138 of the piston 120, as well as by the elasticity of the diaphragm 138. It is further possible to eliminate the outer casing 104 (and thus the gas chamber 106), with the diaphragm 138 simply being exposed, though this arrangement is only preferred where tissue interference is unlikely. As another alternative, the diaphragm 138 could then be substituted with an inflexible wall, and a helical spring, leaf spring, elastomeric spring, or other biasing means could be interposed between the wall and the piston first end 124 to supply the closing force, and with fluid pressure on the piston first end 124 supplying the shunting force. The diaphragm 138 could instead be replaced with an inflexible piston head which travels in the first piston actuation chamber 134 and which is subjected to shunting and closing forces at its fluid side 140 and gas side 142 without any contribution of elastic forces. It is also possible to use a helical spring or other biasing means in conjunction with a diaphragm 138, in which case the diaphragm 138 may supply negligible biasing force, or may supply any desired degree of biasing force in conjunction with the biasing means.

Additionally, in piston-type versions of the shunt (as exemplified by the shunt 100 of FIG. 1), the piston faces upon which the opening and closing pressures act need not be located at an end of the piston. As an example, the piston 120 could have a shaft continuing beyond the gas side 142 of the diaphragm 138 to engage in a bore defined in the casing 104. Such an arrangement would further support the piston 120, but the piston first opening face defined by the diaphragm fluid side 140 and the piston closing face defined at the diaphragm gas side 142 would no longer be situated at an end of the piston 120. (Note that the boundaries of the cutout 130 are not regarded to be piston faces, since fluid pressure on these boundaries does not effect displacement of the piston 120. Stated differently, throughout this document, a "piston face" should be regarded as a surface of the piston whereupon fluid pressure may act to cause displacement of the piston.)

The various shunts may also be used in conjunction with other types of valves (or entire shunts) situated upstream or downstream from the shunt. As an example, some form of one-way valve might be situated at the outlet port to account for situations wherein pressure at the upstream side is sufficiently great to open the valve, but the pressure at the downstream side—which, again, has little or no effect on valve actuation—is even higher than the shunting pressure. In this situation, the valve would open when the shunting pressure is reached at the upstream side, but would then remain open as cerebrospinal fluid flows from the outlet port to the inlet port and the pressure at the upstream side settles to some pressure above the shunting pressure. If a one-way flow valve is situated at the outlet port such that flow from the downstream side of the fluid passage to the upstream side is prohibited, this situation can be prevented or minimized.

The foregoing shunts are designed (or may be designed) to incorporate numerous desired features which have not been emphasized in the foregoing discussion, e.g., the ability to set different shunting pressures before valve opening occurs; ports allowing attachment of ventricular and peritoneal catheters of different lengths; a completely enclosed design whereby tissue ingrowth/encapsulation is avoided or minimized; a completely nonmetallic design whereby imaging artifacts may be avoided; small size and low profile to avoid unnecessary protrusion, and erosion through the slin; a design wherein suture tabs/wings may be added to the casing (or other exterior of the shunt) to more easily allow it to be sutured in place (if desired) to avoid shunt migration; and a design allowing incorporation of radiopaque markers or other tags so that status checks may be performed via X-ray or other diagnostic imaging techniques.

In summary, the invention is not intended to be limited to the preferred versions of the invention described above, and the true scope of the invention will be defined by the claims included in any later-filed utility patent application claiming priority from this provisional patent application.

What is claimed is:

1. A body fluid shunt comprising:
   a. an inlet port;
   b. an outlet port;
   c. a fluid passage between the inlet and outlet ports;
   d. a valve situated between the inlet and outlet ports, the valve defining:
      (1) an upstream side of the fluid passage between the inlet port and the valve, and
      (2) a downstream side of the fluid passage between the valve and the outlet port,
      and wherein the valve is at least partially defined by a drain port extending between the upstream and downstream sides of the fluid passage;
   e. a piston:
      (1) having a piston face defined on the upstream side of the fluid passage, wherein at least a portion of the piston face is defined by a deformable diaphragm,
      (2) being rotationally displaceable to actuate the valve, and
      (3) having a cutout defined therein, the cutout being alignable with the drain port when the piston is displaced,
   wherein:
      i. fluid bearing on the piston face at or above a shunting pressure will displace the piston to actuate the valve, with alignment of the cutout and the drain port opening the valve to thereby allow passage of fluid between the inlet and outlet ports, and
      ii. the position of the piston is independent of the pressure in the downstream side of the fluid passage.

2. The body fluid shunt of claim 1 wherein the deformable diaphragm has opposing sides defining:
   a. a fluid side, the fluid side being at least partially bounded by the upstream side of the fluid passage, and
   b. a gas side, the gas side being at least partially bounded by a gas chamber, the gas chamber being closed to the ingress of fluid.

3. The body fluid shunt of claim 2 wherein the gas chamber has selectively adjustable volume, whereby a user may selectively adjust the gas chamber volume to adjust the pressure of gas therein, and thereby adjust the gas pressure on the gas side of the deformable diaphragm.

4. The body fluid shunt of claim 1 wherein:
   a. the piston is displaceable along a piston travel axis; and
   b. fluid flowing through the valve between the upstream and downstream sides of the flow passage flows along a valve flow direction oriented at least substantially perpendicular to the piston travel axis.

5. The body fluid shunt of claim 1 wherein the piston includes:
   a. a piston tail end opposite its piston face, and
   b. an intermediate length extending between its face and piston tail end, and wherein the downstream side of the fluid passage opens onto the piston only at the intermediate length of the piston.

6. The body fluid shunt of claim 1 wherein the piston has a piston tail end opposite its piston face, and wherein the upstream side of the fluid passage opens onto the piston tail end.

7. The body fluid shunt of claim 1 wherein the deformable diaphragm includes:
   a. a fluid side, the fluid side being at least partially bounded by the upstream side of the fluid passage, and
   b. an opposite side isolated from the upstream side of the fluid passage.

8. The body fluid shunt of claim 7 wherein the opposite side is biased by at least one of:
   a. a compressible gas chamber; and
   b. a spring.

9. The body fluid shunt of claim 7 wherein the opposite side is also isolated from the downstream side of the fluid passage.

10. The body fluid shunt of claim 9 wherein the pressure on the opposite side is adjustable to a fixed level.

11. The body fluid shunt of claim 10 wherein the opposite side is bounded by a gas chamber having selectively adjustable volume, whereby a user may selectively adjust the gas chamber volume to adjust the pressure of gas therein, and thereby adjust the gas pressure on the opposite side of the diaphragm.

12. The body fluid shunt of claim 1 wherein the inlet port is in fluid communication with a brain.

13. The body fluid shunt of claim 1 wherein the outlet port has an elongated flexible catheter extending therefrom.

14. The body fluid shunt of claim 1 wherein:
   a. the inlet port is in fluid communication with a first cavity in a human body, and
   b. the outlet port is in fluid communication with a second cavity in the body.

15. The body fluid shunt of claim 14 wherein the first and second cavities are at different elevations in the body when the body is standing erect.

16. The body fluid shunt of claim 1 wherein the piston is displaced solely by the pressure in the upstream side of the fluid passage.

17. The body fluid shunt of claim 1 wherein:
   a. the fluid passage has a flow axis centrally located along the fluid passage and extending between the inlet and outlet ports;
   b. the piston has a displacement axis along which the piston is displaced, and
   c. the flow axis and displacement axis are non-parallel.

18. The body fluid shunt of claim 17 wherein the flow axis and displacement axis are perpendicular.

19. A body fluid shunt comprising:
   a. an inlet port;
   b. an outlet port;
   c. a fluid passage between the inlet and outlet ports;
   d. a valve situated between the inlet and outlet ports, the valve defining:
      (1) an upstream side of the fluid passage between the inlet port and the valve, and
      (2) a downstream side of the fluid passage between the valve and the outlet port,
      and wherein the valve is at least partially defined by a drain port extending between the upstream and downstream sides of the fluid passage;
   e. a piston displaceable to actuate the valve, the piston having:
      (1) a piston face defined on the upstream side of the fluid passage, at least a portion of the piston face being defined by a deformable diaphragm,
      (2) a deformable mask thereon, the mask deforming to bear against the drain port in accordance with any pressure differential between the upstream and downstream sides of the fluid passage,
      (3) a cutout defined within the deformable mask, the cutout being alignable with the drain port when the piston is displaced,
   wherein:
   i. the valve has:
      (1) a closed state wherein the mask covers the drain port;
      (2) an open state wherein the piston is displaced to move the cutout of the mask into alignment with the drain port,
   ii. fluid bearing on the piston face at or above a shunting pressure will displace the piston to actuate the valve, with alignment of the cutout and the drain port opening the valve to thereby allow passage of fluid between the inlet and outlet ports,
   iii. the position of the piston is independent of the pressure in the downstream side of the fluid passage.

20. The body fluid shunt of claim 19 wherein the mask is a flexible membrane.

21. The body fluid shunt of claim 19 wherein the deformable diaphragm has opposing sides defining:
   a. a fluid side, the fluid side being at least partially bounded by the upstream side of the fluid passage, and
   b. a gas side, the gas side being at least partially bounded by a gas chamber, the gas chamber being closed to the ingress of fluid.

22. The body fluid shunt of claim 21 wherein the gas chamber has selectively adjustable volume, whereby a user may selectively adjust the gas chamber volume to adjust the pressure of gas therein, and thereby adjust the gas pressure on the gas side of the deformable diaphragm.

23. The body fluid shunt of claim 19 wherein:
   a. the piston is displaceable along a piston travel axis; and
   b. fluid flowing through the valve between the upstream and downstream sides of the flow passage flows along a valve flow direction oriented at least substantially perpendicular to the piston travel axis.

24. The body fluid shunt of claim 19 wherein the piston includes:
   a. a piston tail end opposite its piston face, and
   b. an intermediate length extending between its face and piston tail end, and wherein the downstream side of the fluid passage opens onto the piston only at the intermediate length of the piston.

25. The body fluid shunt of claim 19 wherein the piston has a piston tail end opposite its piston face, and wherein the upstream side of the fluid passage opens onto the piston tail end.

26. The body fluid shunt of claim 19 wherein the deformable diaphragm includes:
   a. a fluid side, the fluid side being at least partially bounded by the upstream side of the fluid passage, and
   b. an opposite side isolated from the upstream side of the fluid passage.

27. The body fluid shunt of claim 26 wherein the opposite side is biased by at least one of:
   a. a compressible gas chamber; and
   b. a spring.

28. The body fluid shunt of claim 26 wherein the opposite side is also isolated from the downstream side of the fluid passage.

29. The body fluid shunt of claim 28 wherein the pressure on the opposite side is adjustable to a fixed level.

30. The body fluid shunt of claim 29 wherein the opposite side is bounded by a gas chamber having selectively adjustable volume, whereby a user may selectively adjust the gas chamber volume to adjust the pressure of gas therein, and thereby adjust the gas pressure on the opposite side of the diaphragm.

31. The body fluid shunt of claim 19 wherein the inlet port is in fluid communication with a brain.

32. The body fluid shunt of claim 19 wherein the outlet port has an elongated flexible catheter extending therefrom.

33. The body fluid shunt of claim 19 wherein:
   a. the inlet port is in fluid communication with a first cavity in a human body, and
   b. the outlet port is in fluid communication with a second cavity in the body.

34. The body fluid shunt of claim 33 wherein the first and second cavities are at different elevations in the body when the body is standing erect.

35. A body fluid shunt comprising:
   a. an inlet port;
   b. an outlet port;
   c. a fluid passage between the inlet and outlet ports;
   d. a valve situated between the inlet and outlet ports, the valve defining:
      (1) an upstream side of the fluid passage between the inlet port and the valve, and
      (2) a downstream side of the fluid passage between the valve and the outlet port,
      and wherein the valve is at least partially defined by a drain port extending between the upstream and downstream sides of the fluid passage;
   e. a piston:
      (1) having a piston face defined on the upstream side of the fluid passage, wherein at least a portion of the piston face bears a deformable diaphragm,
      (2) being displaceable to actuate the valve, and
      (3) having a cutout defined therein, wherein:
         i. the cutout is alignable with the drain port when the piston is displaced, and
         ii. the cutout moves along a curved path to align with the drain port when the piston is displaced, wherein:
  i. fluid bearing on the piston face at or above a shunting pressure will displace the piston to actuate the valve, with alignment of the cutout and the drain port opening the valve to thereby allow passage of fluid between the inlet and outlet ports, and
  ii. the position of the piston is independent of the pressure in the downstream side of the fluid passage.

36. The body fluid shunt of claim 35 wherein the inlet port is in fluid communication with a brain.

37. The body fluid shunt of claim 35 wherein the outlet port has an elongated flexible catheter extending therefrom.

38. The body fluid shunt of claim 35 wherein:
  a. the inlet port is in fluid communication with a first cavity in a human body, and
  b. the outlet port is in fluid communication with a second cavity in the body.

39. The body fluid shunt of claim 38 wherein the first and second cavities are at different elevations in the body when the body is standing erect.

40. The body fluid shunt of claim 35 wherein the piston is displaced solely by the pressure in the upstream side of the fluid passage.

41. A body fluid shunt comprising:
  a. an inlet port;
  b. an outlet port;
  c. a fluid passage between the inlet and outlet ports;
  d. a valve situated between the inlet and outlet ports, the valve defining:
    (1) an upstream side of the fluid passage between the inlet port and the valve, and
    (2) a downstream side of the fluid passage between the valve and the outlet port,
    and wherein the valve is at least partially defined by a drain port extending between the upstream and downstream sides of the fluid passage;
  e. a piston:
    (1) having a piston face defined on the upstream side of the fluid passage, wherein:
      i. the piston face is curved, and rides along a complementarily curved guide wall, and
      ii. at least a portion of the piston face bears a deformable diaphragm,
    (2) being displaceable to actuate the valve, and
    (3) having a cutout defined therein, the cutout being alignable with the drain port when the piston is displaced,
  wherein:
    i. fluid bearing on the piston face at or above a shunting pressure will displace the piston to actuate the valve, with alignment of the cutout and the drain port opening the valve to thereby allow passage of fluid between the inlet and outlet ports, and
    ii. the position of the piston is independent of the pressure in the downstream side of the fluid passage.

42. The body fluid shunt of claim 41 wherein the drain port is defined in the guide wall.

43. The body fluid shunt of claim 41 wherein the inlet port is in fluid communication with a brain.

44. The body fluid shunt of claim 41 wherein the outlet port has an elongated flexible catheter extending therefrom.

45. The body fluid shunt of claim 41 wherein:
  a. the inlet port is in fluid communication with a first cavity in a human body, and
  b. the outlet port is in fluid communication with a second cavity in the body.

46. The body fluid shunt of claim 45 wherein the first and second cavities are at different elevations in the body when the body is standing erect.

47. The body fluid shunt of claim 41 wherein the piston is displaced solely by the pressure in the upstream side of the fluid passage.

* * * * *